United States Patent [19]

Kawamura et al.

[11] 4,343,948
[45] Aug. 10, 1982

[54] 2,6-DI-TERT-BUTYL-4-METHYL THIOPYRYLIUM SALT

[75] Inventors: Kouichi Kawamura; Harumi Katsuyama; Hideo Sato, all of Asaka, Japan

[73] Assignee: Fuji Photo Film Co., Ltd., Minami-ashigara, Japan

[21] Appl. No.: 135,030

[22] Filed: Mar. 28, 1980

[30] Foreign Application Priority Data

Mar. 28, 1979 [JP] Japan ................... 54-37249
Jun. 29, 1979 [JP] Japan ................... 54-81523
Jun. 29, 1979 [JP] Japan ................... 54-81524
Jun. 29, 1979 [JP] Japan ................ 54-81525 R

[51] Int. Cl.³ ............... C07D 333/08; C07D 333/32; C07D 333/34
[52] U.S. Cl. .................. 549/13; 542/448; 542/471; 542/454; 549/28; 549/416
[58] Field of Search ................ 549/13, 28; 260/345.9 R; 542/448, 471, 454

[56]    References Cited
U.S. PATENT DOCUMENTS 3,900,582  8/1975  Winter et al. ............. 549/28 X

OTHER PUBLICATIONS

Yur'ev et al., Russian Chemical Reviews, vol. 31, No. 2, pp. 88 and 95-100 (1962).
Yano et al., Chem. Lett. (Japan) 1978, pp. 723-726, (relied upon as abstracted in chemical abstracts, vol. 89, Abst. 178,836, 1978).
Nishino et al., J. Am. Chem. Soc. vol. 101, pp. 5059-5060, Aug. 1979.
Nishino et al., Chem. Abst. vol. 91, Abst. #193148q (1979) (Abst. of Nishino et al. Supra).
Murata et al., Chem. Abstracts, vol. 92, Abst. 180,972z (1980), (Abst. of Murata et al., Hibenzenkei Hokozoku Kagaku Toronkai [Oyobi], Kozo Yuki Kaka ku Toronkai 12th 1979, pp. 77-80 (Japan).

Primary Examiner—Richard Raymond
Attorney, Agent, or Firm—Sughrue, Mion, Zinn, Macpeak and Seas

[57]    ABSTRACT 2,6-Di-tert-butyl-4-methyl thiopyrylium salt of the formula (I):

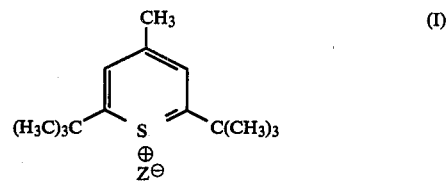

wherein $Z^{\ominus}$ is an anionic function and certain intermediates encountered in its synthesis.

7 Claims, 8 Drawing Figures

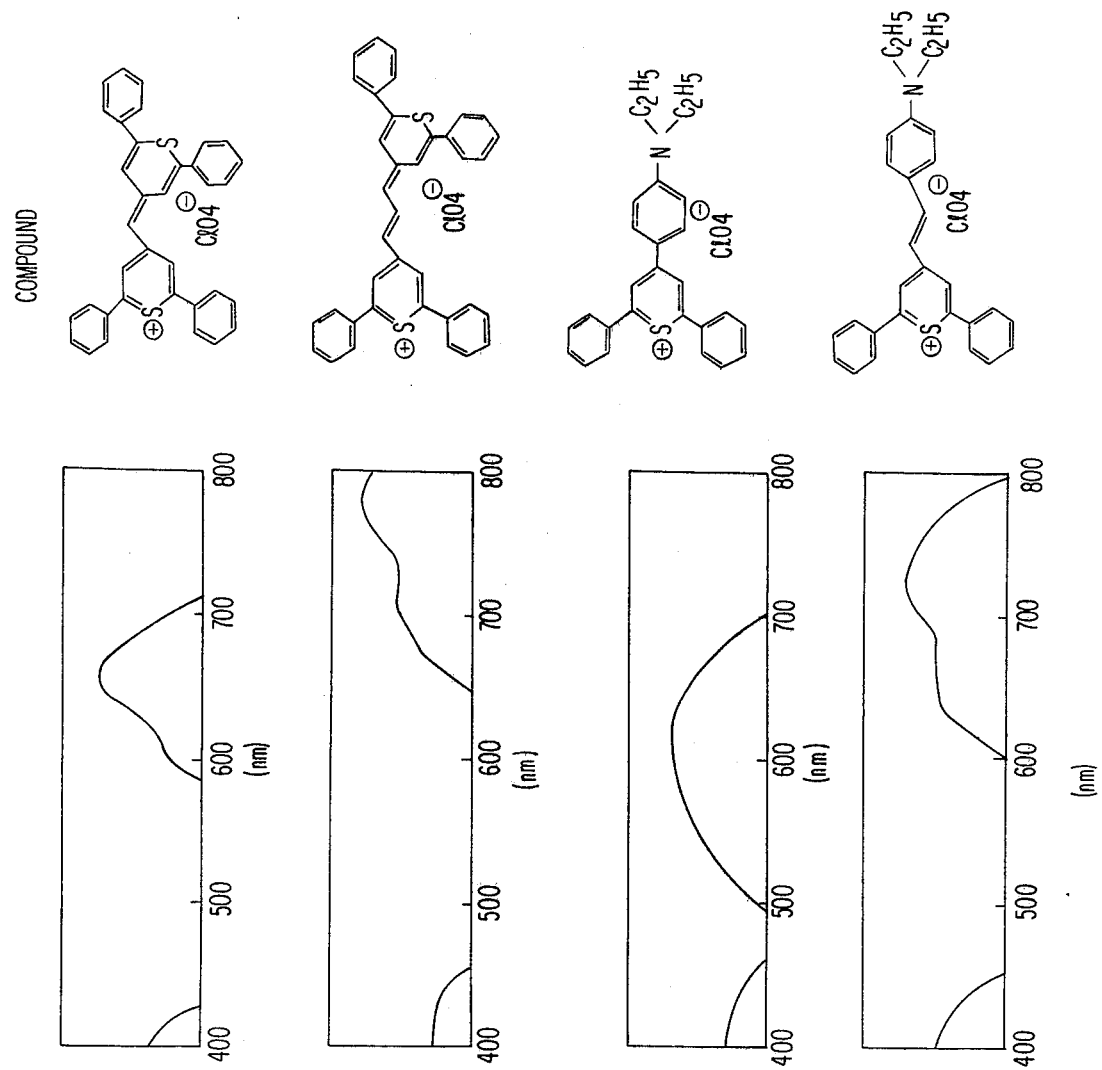

2,6-DI-TERT-BUTYL-4-METHYL THIOPYRYLIUM SALT

BACKGROUND OF THE INVENTION

1. Field of the Invention

This invention relates to a 2,6-di-tert-butyl-4-methyl thiopyrylium salt that can be used as an intermediate for the synthesis of a new type of thiopyrylium dyes.

2. Description of the Prior Art

Thiopyrylium and pyrylium dyes are used for various purposes. For example, as disclosed in Japanese Patent Publication No. 40900/71, they are used in a direct positive photographic silver halide emulsion as an electron acceptor. They are also useful as a spectral sensitizer for a photoconductor, especially an organic photoconductor, as taught in Davis et al., U.S. Pat. No. 3,141,700, Van Allan et al., U.S. Pat. No. 3,250,615, and Reynolds et al., U.S. Pat. No. 3,938,994.

Photoconductors sensitized with thiopyrylium and pyrylium dyes are used in the various applications disclosed in the above mentioned patents, and they are particularly important for use in electrophotography such as xerography or electrofax.

The thiopyrylium dyes that can be synthesized from the compound of this invention are effectively used in not only conventional electrophotography such as xerography or electrofax but also photoelectrophoretic electrophotography. The dyes are particularly useful in color electrophotography using photoconductive particles. It is of course to be understood that the uses of the thiopyrylium dye are not limited to the ones mentioned above.

The principle of the photoelectrophoretic electrophotography is detailed in U.S. Pat. No. 3,384,488, according to which a suspension of electrically photosensitive particles in an insulating liquid is placed between a pair of electrodes, at least one of which is transparent to light and across which a differential voltage is applied, and the suspension is exposed imagewise through the transparent electrode. The electrically photosensitive particles selectively migrate to one electrode to form a visible image on that electrode.

To produce a polychromatic image, a suspension comprising a mixture of a cyan colored particle sensitive to red light, a magenta colored particle sensitive to green light and a yellow colored particle sensitive to blue light is set on the above-described system wherein it is exposed imagewise through a multicolor original image, e.g., a color slide, (or by the reflective printing method) using white light, and one operation of imagewise exposure produces a subtractive color positive image on the transparent electrode.

Illustrative particles suitable for producing such subtractive color images are described in U.S. Pat. No. 3,384,488, Japanese Patent Publication No. 21781/68 (U.S. Pat. Nos. 3,681,064 and 3,384,566) and Japanese Patent Application (OPI) No. 143827/77 (U.S. Pat. No. 4,032,339) (the term "OPI" as used herein refers to a "published unexamined Japanese patent application"), and they are cyan, magenta and yellow pigments the principal absorption bands of which correspond to their principal sensitive regions.

In addition to these three colored photoconductive pigments, U.S. Pat. No. 3,384,488 teaches electrically photosensitive particles which contain a spectral sensitizer so that they are sensitive to radiation in the visible spectral range. The spectral sensitizers must be sensitive selectively to red, green and blue radiation.

As Van Allan et al. and Reynolds et al. patents, supra teach, the thiopyrylium dyes have a high ability to sensitize photoconductors, especially organic photoconductors, but an attempt at performing color copying using the conventional thiopyrylium dyes as a sensitizer for the photoconductive particles has encountered a serious problem. The conventional thiopyrylium dyes that sensitize photoconductive materials for the light in the visible spectrum have a plurality of absorption bands within the visible spectrum, and most of them exhibit absorption to blue radiation. As a result, the sensitizing dyes cause spectral sensitization in the plurality of wavelength bands. Therefore, if the conventional thiopyrylium dye is used as a spectral sensitizer for photosensitive particles to produce a color image from a mixture of three-colored particles by the photoelectrophoretic electrophotography, the resulting image has insufficient color separation, demonstrating the inadequacy of the dye as a spectral sensitizer for use in the photoelectrophoretic electrophotography.

This problem is solved using a new type of thiopyrylium dye that is synthesized from the intermediate provided by this invention.

SUMMARY OF THE INVENTION

This invention provides a 2,6-di-tert-butyl-4-methyl thiopyrylium salt of the formula (I):

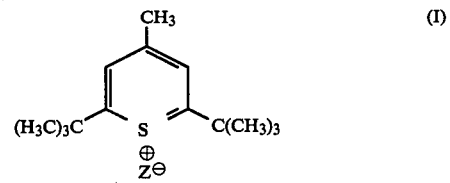

wherein $Z^{\ominus}$ is an anionic function and certain intermediates encountered in its synthesis.

This invention also provides a process for producing a 2,6-di-tert-butyl-4-methyl thiopyrylium salt of the formula (I):

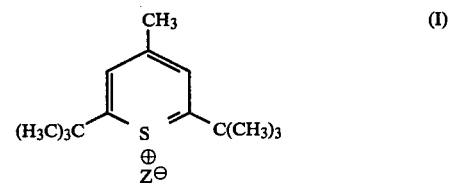

wherein $Z^{\ominus}$ is as defined above.

This invention further provides processes for producing certain intermediates encountered in the synthesis of Compound (I).

BRIEF DESCRIPTION OF THE DRAWINGS

FIGS. 5 to 8 are the spectral sensitivity curves of PVK sensitized spectrally with conventional thiopyrylium dyes.

DETAILED DESCRIPTION OF THE INVENTION

Figures 1, 2, 3, 4:
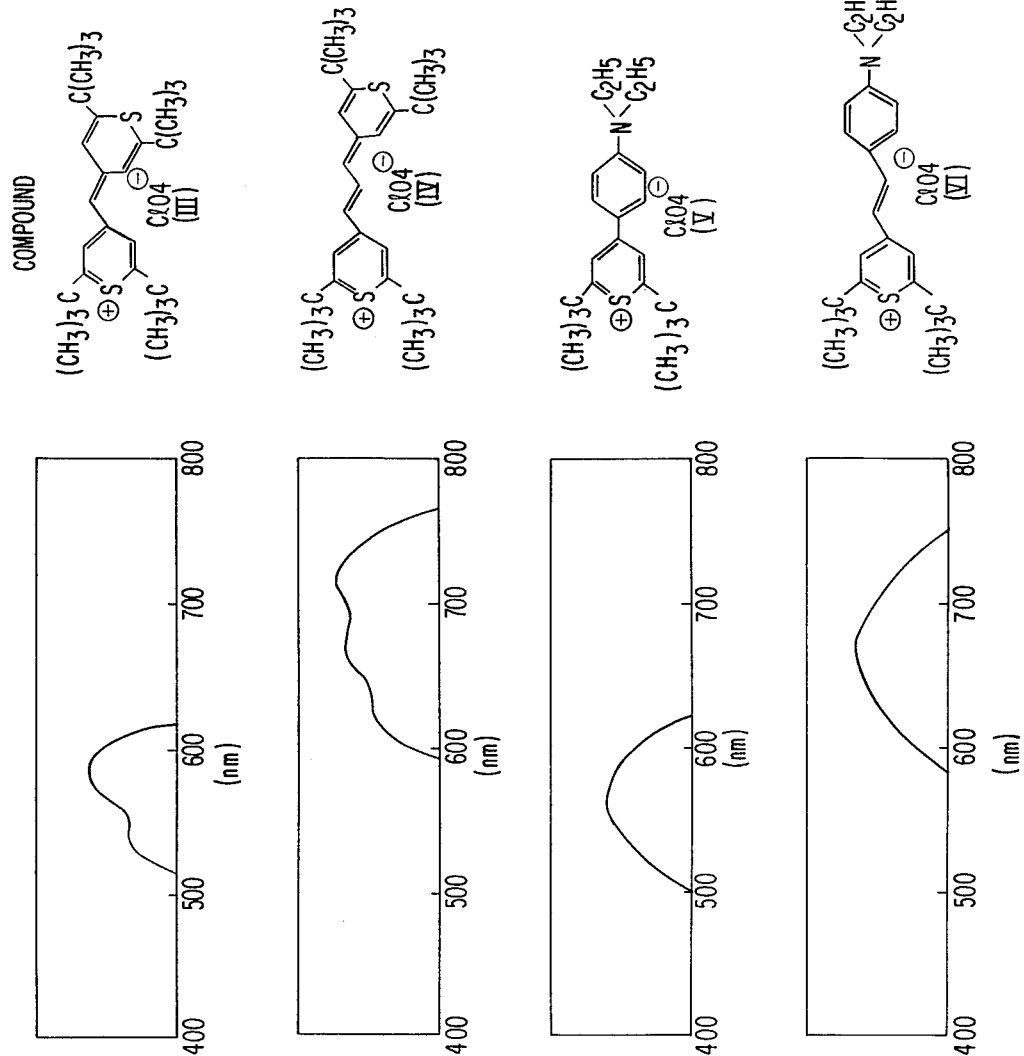
FIGS. 1 to 4 are the spectral sensitivity curves of PVK sensitized spectrally with novel thiopyrylium dyes synthesized from Compound (I) of this invention.

The anionic function $Z^{\ominus}$ of the 2,6-di-tert-butyl-4-methyl thiopyrylium salt of this invention represents well known negatively charged atoms or groups of atoms, and it is preferably an anionic functional group wherein the acid represented by HZ is a strong acid. Illustrative examples of the negatively charged atom as the anionic function include halides such as fluoride, chloride, bromide and iodide.

Illustrative examples of the negatively charged group of atoms as the anionic function include organic anions such as trifluoroacetate, trichloroacetate and p-toluenesulfonate; and inorganic anions such as perchlorate, periodate, tetrachloroaluminate, trichloroferrate (II), tetrafluoroborate, hexafluorophosphate, sulfate, hydrogensulfate and nitrate. For the purposes of this invention, these anionic functions include divalent anions such that half of a divalent anionic function represents a monovalent anionic function. The chloride, bromide, perchlorate, tetrafluoroborate, p-toluenesulfonate, and trifluoroacetate are preferred.

Illustrative novel thiopyrylium dyes that are synthesized from the 2,6-di-tert-butyl-4-methyl thiopyrylium salt of this invention are represented by the following formulae (III) thru (VI):

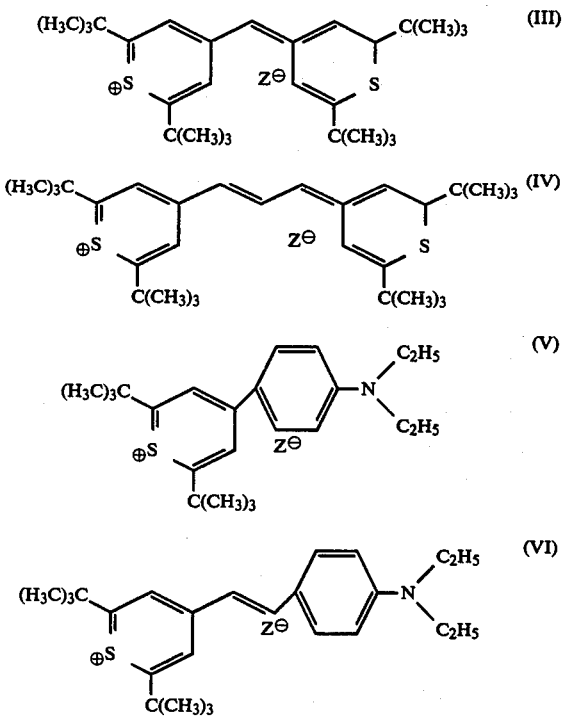

wherein $Z^{\ominus}$ is the same as defined above.

FIGS. 1 thru 4 are the spectral sensitivity curves of poly-N-vinyl-carbazole (PVK) as sensitized spectrally by novel thiopyrylium dyes synthesized from Compound (I) of this invention. FIGS. 5 thru 8 are the spectral sensitivity curves of PVK as sensitized spectrally by conventional thiopyrylium dyes. As comparisons between FIGS. 1 and 5, between FIGS. 2 and 6, between FIGS. 3 and 7, and between FIGS. 4 and 8 clearly show, due to the presence of a tert-butyl group at the 2- and 6-positions of the thiopyran ring, the novel thiopyrylium dye differs from the conventional thiopyrylium dye having an aryl group in that it does not exhibit a secondary absorption at near 400 nm and that it is only sensitive to red or green radiation. Therefore, a photoconductive composition containing the novel thiopyrylium dye as a spectral sensitizer is not sensitive to blue light in the visible spectrum, especially to light at a wavelength in the range of from 400 to 450 nm.

Consequently, unlike photosensitive particles prepared in the presence of the conventional thiopyrylium dyes, photosensitive particles for color photoelectrophoretic electrophotography that contain the new type of thiopyrylium dyes as a spectral sensitizer provide improved color separation from blue sensitive yellow particles. Color photoelectrophoretic electrophotographic processing of a mixture of three-colored particles comprising yellow and magenta particles plus a cyan particle that contains Compound (IV) as a sensitizing dye for the red region provides an image exhibiting distinct color separation from the yellow particles.

Some of the new type of thiopyrylium dyes synthesized from Compound (I) of this invention are included within the formulae disclosed in the prior patents mentioned hereinabove, but none of them are specifically described, nor has Compound (I) been known to date. Furthermore, these patents neither teach nor suggest the fact that the new type of thiopyrylium dyes are red- or green-sensitive dyes having no secondary absorption in the blue region. For these reasons, the compound of this invention constitutes an invention which is clearly distinguished from any of the inventions described in the aforementioned prior patents.

The 2,6-di-tert-butyl-4-methyl thiopyrylium salt of this invention can be synthesized by treating 2,6-di-tert-butyl-4H-thiopyran-4-one (Compound (II)) with a Grignard reagent in a solvent in an oxygen-free atmosphere, followed by treatment with an acid which is capable of forming an anionic function through dissociation and which is expressed by the formula, HZ, such as hydrochloric acid, hydrobromic acid, tetrafluoroboric acid, perchloric acid, p-toluenesulfonic acid, trifluoroacetic acid, etc.

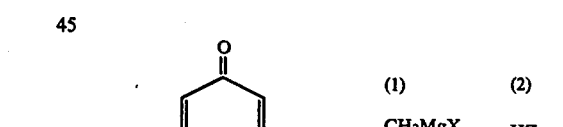

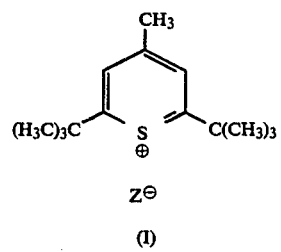

X in formula (II) is iodide, bromide or chloride; HZ is an acid that is capable of forming an anionic function through dissociation and $Z^{\ominus}$ is an anionic function, e.g., chloride, bromide, tetrafluoroborate, perchlorate, p-toluenesulfonate, trifluoroacetate, etc.

Preferred examples of the Grignard reagent are methylmagnesium iodide, methylmagnesium bromide and methylmagnesium chloride. These Grignard reagents may be replaced by other organometallic compounds such as methylpotassium, methylsodium, methyllithium, methylcalcium iodate, dimethylberyllium, trimethylaluminum, and trimethylboron.

A non-aqueous solvent substantially free from water may be used as the solvent. Illustrative solvents include ether type compounds such as dimethyl ether, methyl ethyl ether, diethyl ether, dimethoxyethane, tetrahydrofuran and 1,4-dioxane; aromatic compounds such as benzene and toluene; and saturated hydrocarbon compounds such as pentane, hexane, cyclohexane, methylcyclohexane and petroleum ether. A suitable amount of the solvent which can be used is about 1 to 1,000 ml, preferably about 10 to 100 ml per gram of the compound of the formula (II).

To activate the organometallic compound, the solvent may contain hexamethylphosphoric triamide, N,N,N',N'-tetramethylethylenediamine, or 1,4-diazabicyclo[2,2,2]octane.

The reaction temperature and time depend largely upon the type of the organometallic compound and the solvent used. If the solvent is diethyl ether and the organometallic compound is methylmagnesium iodide, a suitable reaction temperature is in the range of from $-20°$ C. to about $25°$ C., and a suitable reaction time is in the range of from about 30 minutes to about 90 minutes. The organometallic compound is used in an amount between 1 mol and about 10 mols, preferably between 1 mol and about 3 mols, per mol of Compound (II).

By the term "oxygen-free atmosphere" is meant rare gas typified by helium and argon as well as an inert gas typified by nitrogen. These gases replace air to form a substantially oxygen-free condition under which the reaction is carried out. The pressure of the rare gas or inert gas may be in the neighborhood of atmospheric pressure, but this is just one example of the reaction pressure and suitable values may be selected depending on the case.

The intermediate obtained by treating Compound (II) with the organometallic compound is 2,6-di-tert-butyl-4-hydroxy-4-methyl-4H-thiopyran which is represented by the formula (VII):

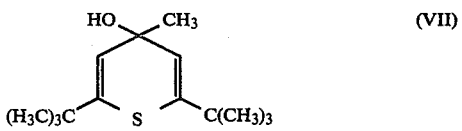

In the process of manufacturing Compound (I) of this invention, Compound (VII) need not be separated but is immediately treated with an acid to provide a high yield of Compound (I) as a precipitate in the solvent. One significant characteristic of the process for producing Compound (I) of this invention is its ability to realize high yield production and easy separation of the end compound.

Illustrative acids that can be used in the process for producing Compound (I) of this invention include hydrofluoric acid, hydrochloric acid, hydrobromic acid, hydriodic acid, perchloric acid, periodic acid, tetrafluoroboric acid, hexafluorophosphoric acid, sulfuric acid, nitric acid, trifluoroacetic acid, trichloroacetic acid, and p-toluenesulfonic acid. Preferred acids are hydrochloric acid, hydrobromic acid, perchloric acid, tetrafluoroboric acid, trifluoroacetic acid, and p-toluenesulfonic acid. The Z of the acid (HZ) serves as the anionic function of Compound (I).

Alternatively, Compound (I) can be manufactured by the process described in A. I. Tolmachev et al., *Ukrainskii Khimicheskii Zhurnal,* Vol. 40, pp. 287–289 (1974), according to which Compound (II) is treated with a cyanoacetic ester, and the resulting adduct is treated with an acid to effect hydrolysis to thereby provide the end compound.

Compound (II) is a novel compound and it can be synthesized in the following four steps from the 2,6-di-tert-butyl-4H-pyran-4-one of the formula (VIII) which in turn can be synthesized by the method described in G. A. Reynolds et al., *Journal of Heterocyclic Chemistry,* Vol. 11, p. 1075 (1974):

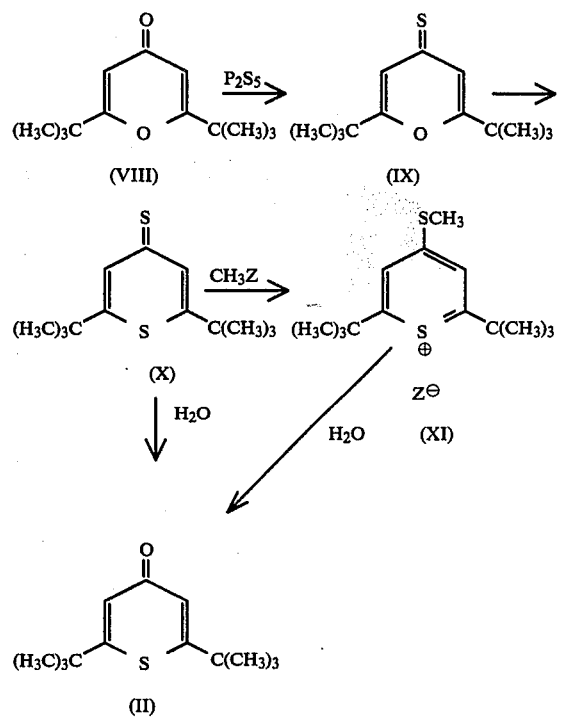

This synthesis is explained in detail below.

Synthesis of Compound (IX)

Above, 2,6-di-tert-butyl-4H-pyran-4-thione, Compound (IX), also a novel compound, can be synthesized by heating 2,6-di-tert-butyl-4H-pyran-4-one, Compound (VIII), in the presence of phosphorous pentasulfide.

Example 1 illustrates the preparation of Compound (IX) from Compound (VIII).

EXAMPLE 1

34.6 g of 2,6-di-tert-butyl-4H-pyran-4-one was dissolved in 240 ml of anhydrous benzene, and 73 g of phosphorus pentasulfide was added thereto. The mixture was heated at the reflux temperature for 2.5 hours while stirring.

After completion of the reaction, the benzene solution was removed by decantation. Aqueous ammonia was added to the residue to decompose the phosphorus pentasulfide, followed by extracting with diethyl ether and drying over anhydrous sodium sulfate. The solvent was distilled off under reduced pressure from the benzene solution, and the residue was extracted with hexane and concentrated to obtain 16.0 g of a reddish crystal. The ethereal extract and an oily material having not been extracted with hexane were combined and passed through a silica gel column (eluent:benzene) to thereby purify the product. Thus, 6.8 g of a crystal was further obtained.

Total Yield: 22.8 g (61%)

Melting Point: 108°–108.5° C., flesh tint colored crystal recrystallized from hexane Elemental Analysis: Calculated for $C_{13}H_{20}OS$: C, 69.59%; H, 8.99%; S, 14.29%. Found: C, 69.51%; H, 9.00%; S, 14.26%.

Mass Analysis (m/e): 224 (100%), 209 (10%), 165 (56%)

I.R. Spectrum: 1630, 1305 $cm^{-1}$

N.M.R. Spectrum: (chemical shift, ppm, tetramethylsilane)

(proton) 99.6 MHz in deuteroacetonitrile 1.30, 6.99 (each singlet, area ratio=9:1)

(carbon 13) 25.5 MHz in deuterochloroform 202.83, 168.49, 120.51, 36.09, 27.79

U.V. and Visible Spectrum: (nm, log $\epsilon$ in parentheses, in cyclohexane) 248 (3.96), 338 (4.30), 526 (1.35), 556 (1.15)

Synthesis of Compound (X)

2,6-Di-tert-butyl-4H-thiopyran-4-thione, Compound (X), can be synthesized by reacting 2,6-di-tert-butyl-4H-pyran-4-thione, Compound (IX), with an alkali metal hydrosulfide, an alkali metal sulfide, MSH or $M_2S$, in a highly polar, non-aqueous solvent and an inert atmosphere.

Any of potassium hydrosulfide, sodium hydrosulfide and lithium hydrosulfide can be used as the alkali metal hydrosulfide in the reaction, but sodium hydrosulfide is preferred for its commercial availability. Representative examples of alkali metal sulfides which can be used instead of the alkali metal hydrosulfide include sodium sulfide, potassium sulfide, lithium sulfide, etc. The alkali metal hydrosulfide and alkali metal sulfide are used in an amount of about 1 to 30 and preferably about 3 to 20 molar equivalents based on Compound (IX).

The solvent used is preferably one having a dielectric constant ($\epsilon$) of 20 or more and a dipole moment ($\mu$) of 2 or more. Particularly, preferred solvents have a dielectric constant of about 25 to 200 and a dipole moment of about 3 to 5. [For a discussion of dielectric constants and dipole moments as discussed above, see J. A. Riddick et al., *Techniques of Chemistry*, Vol. II, "Organic Solvents", 3rd Printing, Wiley-Interscience (1970).] Suitable examples of the solvent are hexamethylphosphoric triamide, dimethyl sulfoxide, N,N-dimethylformamide, N-methylpyrrolidone, and the like. Hexamethylphosphoric triamide is preferred. The amount of solvents varies with the alkali metal hydrosulfide or sulfide used but generally ranges from about 5 to 100 ml, preferably from about 10 to 50 ml, per gram of the alkali metal hydrosulfide or sulfide.

As mentioned, the reaction is carried out in an inert (oxygen-free) atmosphere. Suitable atmospheres are nitrogen, argon, and carbon dioxide. Preferably the inert atmosphere is obtained by replacing any air in the reaction vessel with the inert gas and continuously flowing an inert gas stream through the vessel during the reaction at a flow rate at which oxygen by-products are not produced (e.g., about 0.01 to 2 l/min and more preferably about 0.1 to 1 l/min). If the reaction is carried out in the presence of air or oxygen, by-products are easily formed which reduce the yield of the desired compound.

The reaction of Compound (IX) is preferably carried out at a temperature of about 50° to 200° C. To increase the reaction rate without decomposing the desired compound, a temperature of about 80° to 120° C. is preferred. The reaction time can vary from 30 minutes to 10 hours but usually runs about 1 to 3 hours. The best yields are obtained when the reaction is carried out in hexamethylphosphoric triamide at a temperature of 85° to 90° C. for 1.5 hours. Preferably the reaction is carried out at atmospheric pressure, however, super atmospheric pressures up to 200 atms can be used.

Because 2,6-di-tert-butyl-4H-thiopyran-4-thione has the stereochemically bulky tert-butyl groups at the 2- and 6-positions, conventional synthetic approaches have not been found applicable to its synthesis. Thus, an apparently analogous method in which 2,6-dimethyl-4H-thiopyran-4-thione is prepared by reacting 2,6-dimethyl-4H-pyran-4-thione with 50% potassium hydrosulfide under an ethanol reflux fails to yield the compound. [The aforementioned method is disclosed by F. Arndt et al., *Rev. Faculté Sci. Univ. Istanbul*, A13, 57–77 (1948); *Chemical Abstracts*, 42, 4176i (1948).] Even when the aforementioned reaction is prolonged, no amount of 2,6-di-tert-butyl-4H-thiopyran-4-thione is obtained. The inventors, however, have discovered that by conducting the reaction in the presence of a highly polar, non-aqueous solvent such as hexamethylphosphoric triamide, the corresponding 2,6-di-tert-butyl thiopyran compound is obtained in good yield.

The following Examples 2 to 4 illustrate the preparation of 2,6-di-tert-butyl-4H-thiopyran-4-thione from the corresponding pyran.

EXAMPLE 2

6.64 g of 2,6-di-tert-butyl-4H-pyran-4-thione was dissolved in 330 ml of hexamethylphosphoric triamide, and an argon gas was passed therethrough for 20 minutes.

The mixture was stirred on an oil bath at 85°–90° C., and 19.8 g of sodium hydrosulfide (prepared by vacuum drying about 70% $NaSH.xH_2O$ (a product of Wako Pure Chemical Industries, Ltd.) over phosphorus pentoxide at 70°–80° C. for one day) was added thereto in an argon atmosphere over a period of time of 30 minutes.

The stirring was continued at the same temperature for 1.5 hours, and the reaction solution was thrown into water whereby the reaction completed. The thus-formed crystal was filtered, dried and recrystallized from hexane.

Yield: 1.78 g (25%)

Melting Point: 162° C., red crystal

Elemental Analysis: Calculated for $C_{13}H_{20}S_2$: C, 64.94%; H, 8.39%; S, 26.67%. Found: C, 64.73%; H, 8.44%; S, 26.75%.

Mass Analysis (m/e): 240 (100%), 225 (65%), 181 (40%)

I.R. Spectrum: 1570, 1125 $cm^{-1}$

N.M.R. Spectrum: (chemical shift, ppm, tetramethylsilane)

(proton) 99.6 MHz in deuterochloroform 1.43, 7.88 (each singlet, area ratio=9:1)

(carbon 13) 25.5 MHz in deuterochloroform 201.83, 158.89, 134.85, 38.32, 30.53

U.V. and Visible Spectrum: (nm, log $\epsilon$ in parentheses, in cyclohexane) 263 (3.76), 3.80 (4.35), 569 (1.55), 612 (1.26)

EXAMPLE 3

The same procedure as in Example 2 was followed except that N-methylpyrrolidone was used in place of hexamethylphosphoric triamide to thereby obtain a red crystal in a yield of 10%. The thus-obtained crystal was confirmed to have the same I.R. spectrum as the product obtained in Example 2.

EXAMPLE 4

The same procedure as in Example 2 was followed except that 20.0 g of KSH, 19.5 g of LiSH and 22.3 g of Na$_2$S were used in place of 19.8 g of sodium hydrosulfide, respectively, to thereby obtain a red crystal in a yield of 20%, 30% and 15%, respectively. The respective crystal was confirmed to have a melting point of 162° C., 160° C. and 159° C. and have the same I.R. spectrum as the product obtained in Example 2.

Synthesis of Compound (XI)

2,6-Di-tert-butyl-4-(methylthio)thiopyrylium salt, Compound (XI), is synthesized by methylating the 2,6-di-tert-butyl-4H-thiopyran-4-thione, Compound (X), obtained as above. The methylating agent can be represented by the formula CH$_3$Z and represents compounds such as methyl iodide, methyl bromide, dimethyl sulfate, trimethyloxonium tetrafluoroborate, methylfluorosulfate, etc., with methyl iodide and dimethyl sulfate being preferred for their handling ease.

The reaction can be performed in any solvent which is capable of dissolving Compound (X) and the methylating agent. Representative examples are ketones (e.g., acetone, methyl ethyl ketone, etc.), acetonitrile, and halogenated hydrocarbons (e.g., chloroform, etc.). The reaction can be performed in the methylating agent without a solvent, if desired. When the solvent is used, the amount varies depending on the starting materials and generally ranges from about 1 to 100 ml and preferably from about 5 to 20 ml per gram of Compound (X).

The methylating agent is typically used in an amount of about 1 to 50 and preferably about 1 to 20 molar equivalents based on Compound (X). Methyl iodide is preferably used in about 1 to 30 molar equivalents. If the methylating agent is used in an amount less than 1 molar equivalent, the reaction yield becomes too low. On the other hand, if methyl iodide is used in an amount more than 30 molar equivalents, an improvement in yield is not observed. In general amounts of 2 to 10 molar equivalents are optimum from the standpoint of yield and economy.

The reaction temperature and time vary with the type of methylating agent and solvent used. A suitable reaction temperature is about −10° C. to the refluxing temperature of the methylating agent or solvent and is preferably about 0° C. to the refluxing temperature. Of course, it is most convenient in terms of the speed of the reaction and the yield to perform the reaction at room temperature to 200° C. and most preferably at 40° C. to 100° C. The reaction time varies from about 5 minutes to 5 hours and is preferably about 30 minutes to 2 hours. Using methyl iodide as the methylating agent and acetone as the solvent, the reaction is preferably carried out under refluxing conditions for 30 minutes to 1 or 2 hours.

The following Example 5 illustrates the preparation of 2,6-di-tert-butyl-4-(methylthio)thiopyrylium iodide, Compound (XI).

EXAMPLE 5

1.55 g of 2,6-di-tert-butyl-4H-thiopyran-4-thione was refluxed together with 20 ml of acetone and 5 ml of methyl iodide for 1 hour.

After the solvent was distilled off under reduced pressure, the residue was recrystallized from acetone to obtain 1.55 g (yield: 63%) of a prism-like red crystal having a melting point of 150° C. to 155° C. (decomposed).

Elemental Analysis:

Calculated for C$_{14}$H$_{23}$S$_2$I: C, 43.98%; H, 6.06%; S, 16.77%. Found: C, 43.87%; H, 6.14%; S, 16.53%.

I.R. Spectrum: 1567, 1475, 1118 cm$^{-1}$

N.M.R. Spectrum: (chemical shift, ppm, tetramethylsilane)

(proton) 99.6 MHz in deutero dimethyl sulfoxide 1.59, 3.06, 8.44 (each singlet, area ratio=18:3:2)

(carbon 13) 25.5 MHz in deutero dimethyl sulfoxide 177.13, 172.29, 126.89, 41.01, 30.19, 15.50

U.V. and Visible Spectrum: (nm, log $\epsilon$ in parentheses, in chloroform) 271 (3.95), 303 (3.68), 365 (4.35), 482 (2.95)

Synthesis of Compound (II)

Compound (II) is obtained by hydrolyzing either the methylthio-thiopyrylium salt, Compound (XI) or 2,6-di-tert-butyl-4H-thiopyran-4-thione, Compound (X). The hydrolysis of Compound (XI) provides better yields than the hydrolysis of Compound (X).

Hydrolysis is carried out in water or a highly polar solvent which is miscible with water. In addition to the highly polar solvents described above in the synthesis of Compound (X), water, alcohols (e.g., methanol, ethanol, ethylene glycol, etc.), ethers (e.g., tetrahydrofuran, 1,4-dioxane, etc.), acetonitrile, acetone and sulfolane can be used. The amount of the solvent varies with the starting material but generally ranges from about 1 to 100 equivalents by weight, preferably about 1 to 20 equivalents by weight based on Compound (XI) or (X). When a solvent other than water is used, water must be added to the reaction system in amounts of about 0.001 part by weight or more, preferably about 0.001 to 10 equivalents by weight, more preferably about 0.01 to 0.5 equivalent by weight based on the solvent.

The reaction can be carried out at temperatures from room temperature to refluxing temperatures. In order to obtain a good reaction rate and avoid decomposition of the products, the reaction is preferably carried out at temperatures of about 80° to 100° C. The optimum reaction time varies with the solvent and reaction temperature but generally ranges from about 10 minutes to 10 hours. When the reaction is carried out using dimethyl sulfoxide as the solvent, the reaction is carried out at 85° to 90° C. for about 30 minutes to 5 hours and preferably for about 1 to 3 hours.

The reaction can be carried out in the presence of an acid, base or other catalyst. Suitable examples are acids having a dissociation constant in water (pKa) of 5 or less such as hydrochloric acid, trifluoroacetic acid, p-toluenesulfonic acid, etc. The alkali catalyst preferably has a pKa (of its conjugated acid) of 9 or more. Representative examples are ammonia, sodium hydroxide, triethylamine, etc. In addition to the above catalyst, mercuric chloride, silver carbonate, lead acetate, mercuric oxide, etc., can be used.

The following example 6 illustrates the preparation of Compound (II).

EXAMPLE 6

1.30 g of 2,6-di-tert-butyl-4-(methylthio)thiopyrylium iodide was allowed to stir on an oil bath at 85° to 90° C. together with 10 ml of dimethyl sulfoxide and 1 ml of water for 3 hours.

The reaction solution was thrown into water, and the mixture was extracted with diethyl ether. The diethyl ether solution was dried over anhydrous sodium sulfate, and the solvent was distilled off under reduced pressure. The residue was passed through an alumina column using a benzene-diethyl ether (1:1) mixed solvent to thereby obtain 740 mg (yield: 97%) of a crystal. The thus-obtained crystal was recrystallized from cyclohexane to obtain a colorless crystal having a melting point of 97° to 98° C.

Elemental Analysis:
Calculated for $C_{13}H_{20}SO$: C, 69.59%; H, 8.99%; S, 14.29%. Found: C, 69.13%; H, 9.06%; S, 14.41%.

Mass Analysis (m/e): 224 (30%), 181 (100%)

I.R. Spectrum: 1610, 1348, 880, 730 cm$^{-1}$

N.M.R. Spectrum: (chemical shift, ppm, tetramethylsilane)
(proton) 99.6 MHz in deuterochloroform 1.38, 6.90 (each singlet, area ratio=9:1)
(carbon 13) 25.5 MHz in deuterochloroform 183.00, 165.38, 124.32, 38.38, 30.54

U.V. and Visible Spectrum: (nm, log ε in parentheses, in cyclohexane) 222 (3.85), 285 (4.17), 329 (1.57), 363 (0.96)

The synthesis of Compound (I) from Compound (II) is now described in greater detail by reference to the following example which is no given here for illustrative purposes only and is by no means intended to limit the scope of the invention.

EXAMPLE 7

2,6-Di-tert-butyl-4-methyl thiopyrylium perchlorate [Compound (I)]

2,6-Di-tert-butyl-4H-thiopyran-4-one (550 mg) was dissolved in 20 ml of diethyl ether in an argon atmosphere, then 8.6 ml of a solution of methylmagnesium iodide in diethyl ether (2.7 mmol) was added dropwise to the solution under cooling at about −10° C. After the addition, the mixture was stirred for a period of 45 minutes at room temperature (ca. 23° C.), followed by addition of a saturated aqueous solution of ammonium chloride. The ether solution was decanted, ether was distilled under vacuum, 20 ml of 35% perchloric acid was added to the residue, and the mixture was warmed on a water bath to produce a crystal. The crystal was filtered, washed with cold water, washed with diethyl ether and dried. The yield was 470 mg (63%). Recrystallization from ethanol gave a colorless crystal having a melting point between 192° and 193° C. Elemental analysis and spectral analysis of the crystal showed that it was Compound (I).

Elemental Analysis:
Calculated for $C_{14}H_{23}ClO_4S$: C, 52.08%; H, 7.18%; S, 9.93%. Found: C, 52.00%; H, 7.23%; S, 9.75%.

I.R. Spectrum: 1590, 1375, 1085 cm$^{-1}$

N.M.R. Spectrum: (chemical shift, ppm, tetramethylsilane)
(proton) 99.6 MHz in hexadeuteroacetone (acetone-d$_6$) 1.67, 2.96, 8.81 (each singlet, area ratio=18:3:2)
(carbon 13) 25.5 MHz in hexadeuteroacetone (acetone-d$_6$) 184.87, 167.08, 134.67, 42.53, 31.18, 28.75

U.V. and Visible Spectrum: (nm, log ε in parentheses, in acetonitrile) 302 (3.97), 262 (3.88), 213 (4.47)

While the invention has been described in detail and with reference to specific embodiments thereof, it will be apparent to one skilled in the art that various changes and modifications can be made therein without departing from the spirit and scope thereof.

What is claimed is:

1. A compound of the formula:

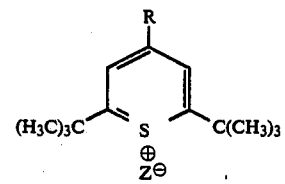

where R is —SCH$_3$ or —CH$_3$ and Z$^\ominus$ is an anionic function wherein the acid represented by HZ is a strong acid.

2. The 2,6-di-tert-butyl-4-methyl thiopyrylium salt of claim 1:

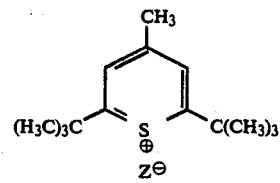

wherein Z$^\ominus$ is an anionic function.

3. The compound of claim 2, wherein Z$^\ominus$ represents a halide.

4. The compound of claim 2, wherein Z$^\ominus$ represents trifluoroacetate, trichloroacetate, or p-toluenesulfonate.

5. The compound of claim 2, wherein Z$^\ominus$ represents perchlorate, periodate, tetrachloroaluminate, trichloroferrate (II), tetrafluoroborate, hexafluorophosphate, sulfate, hydrogensulfate, or nitrate.

6. A compound of the formula:

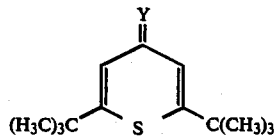

where Y is O or S.

7. A compound of the formula:

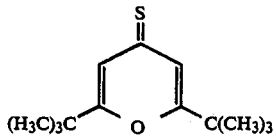

* * * * *